US011896517B2

(12) United States Patent
Czaplewski et al.

(10) Patent No.: US 11,896,517 B2
(45) Date of Patent: Feb. 13, 2024

(54) ADJUSTABLE CONVEXITY OSTOMY BARRIER

(71) Applicant: Hollister Incorporated, Libertyville, IL (US)

(72) Inventors: Gregory J. Czaplewski, Glendale Heights, IL (US); Kenneth Nielsen, Alsgarde (DK); Christen Grum-Schwensen, Hillerod (DK); Ryan S. Park, Northbrook, IL (US); Tuan Tran, Genoa City, WI (US); Brian T. Leadingham, Pleasant Prairie, WI (US); Patrick C. Tetzlaff, Caledonia, WI (US)

(73) Assignee: Hollister Incorporated, Libertyville, IL (US)

( * ) Notice: Subject to any disclaimer, the term of this patent is extended or adjusted under 35 U.S.C. 154(b) by 663 days.

(21) Appl. No.: 16/329,331

(22) PCT Filed: Oct. 3, 2017

(86) PCT No.: PCT/US2017/054903
§ 371 (c)(1),
(2) Date: Feb. 28, 2019

(87) PCT Pub. No.: WO2018/067539
PCT Pub. Date: Apr. 12, 2018

(65) Prior Publication Data
US 2019/0231580 A1 Aug. 1, 2019

Related U.S. Application Data

(60) Provisional application No. 62/403,449, filed on Oct. 3, 2016.

(51) Int. Cl.
A61F 5/448 (2006.01)
A61F 5/445 (2006.01)
A61F 5/443 (2006.01)

(52) U.S. Cl.
CPC .............. *A61F 5/448* (2013.01); *A61F 5/443* (2013.01); *A61F 5/445* (2013.01); *A61F 2005/4483* (2013.01)

(58) Field of Classification Search
CPC .......... A61F 5/443; A61F 5/448; A61F 5/445; A61F 2005/4483
See application file for complete search history.

(56) References Cited

U.S. PATENT DOCUMENTS 2,874,697 A * 2/1959 Johnson .................. A61F 5/448
604/340
4,137,918 A * 2/1979 Bogert ..................... A61F 5/445
604/328

(Continued)

FOREIGN PATENT DOCUMENTS

EP 0317326 A2 5/1989
EP 1348412 A1 * 10/2003 ............. A61F 5/445

(Continued)

OTHER PUBLICATIONS

International Preliminary Report on Patentability issued by IB of WIPO in connection with PCT/US2017/054903 dated Apr. 18, 2019.

(Continued)

*Primary Examiner* — Benjamin J Klein
*Assistant Examiner* — Ted Yang
(74) *Attorney, Agent, or Firm* — Levenfeld Pearlstein, LLC

(57) ABSTRACT

An ostomy barrier appliance for attaching an ostomy appliance to peristomal skin surrounding a stoma is provided. The (Continued)

ostomy barrier appliance includes a skin barrier, an inlet opening for receiving a stoma, and a convexity adjusting device arranged adjacent the skin barrier. The convexity adjusting device is configured to adjust the convexity of the skin barrier.

5 Claims, 10 Drawing Sheets

(56) References Cited

U.S. PATENT DOCUMENTS

| | | | |
|---|---|---|---|
| 4,592,750 A | 6/1986 | Kay | |
| 4,596,566 A * | 6/1986 | Kay | A61F 5/4404 604/176 |
| 4,834,731 A * | 5/1989 | Nowak | A61F 5/448 604/339 |
| 5,004,464 A * | 4/1991 | Leise, Jr. | A61F 5/448 604/338 |
| 5,429,625 A * | 7/1995 | Holmberg | A61F 5/448 604/338 |
| 5,501,678 A * | 3/1996 | Olsen | A61F 5/443 604/344 |
| 5,618,276 A * | 4/1997 | Leise, Jr. | A61F 5/445 604/338 |
| 6,210,384 B1 * | 4/2001 | Cline | A61F 5/448 604/338 |
| 6,673,056 B2 | 1/2004 | Metz et al. | |
| 2003/0073965 A1 * | 4/2003 | Leise, Jr. | A61F 5/448 604/338 |
| 2003/0088219 A1 * | 5/2003 | Metz | A61F 5/448 604/339 |
| 2003/0171737 A1 * | 9/2003 | Leise, Jr. | A61F 5/448 264/40.1 |
| 2008/0269698 A1 * | 10/2008 | Alexander | A61F 5/445 604/332 |
| 2008/0275402 A1 * | 11/2008 | Schnell | A61F 5/445 604/175 |
| 2009/0163883 A1 * | 6/2009 | Christensen | A61F 5/441 604/328 |
| 2010/0174253 A1 * | 7/2010 | Cline | A61F 5/445 604/328 |
| 2011/0092929 A1 * | 4/2011 | Weig | A61F 5/445 604/338 |
| 2011/0218507 A1 * | 9/2011 | Andersen | A61F 5/445 604/338 |
| 2012/0323192 A1 * | 12/2012 | Willoughby | A61F 5/445 604/337 |
| 2013/0304008 A1 * | 11/2013 | Hanuka | A61F 5/445 604/338 |
| 2014/0163496 A1 * | 6/2014 | Grum-Schwensen | A61J 1/00 604/338 |
| 2014/0316360 A1 * | 10/2014 | Ekfeldt | A61F 5/445 604/338 |
| 2014/0324002 A1 * | 10/2014 | Luce | A61F 5/441 604/338 |
| 2015/0164679 A1 * | 6/2015 | Maidl | A61F 5/445 604/332 |
| 2015/0297389 A1 * | 10/2015 | Nyberg | A61F 5/443 604/344 |
| 2016/0051394 A1 * | 2/2016 | Nielsen | A61F 5/445 604/338 |

FOREIGN PATENT DOCUMENTS

| | | | | |
|---|---|---|---|---|
| EP | 1348412 A1 | 10/2003 | | |
| EP | 1389136 B1 * | 10/2005 | | A61F 5/448 |
| EP | 2601915 A1 | 6/2013 | | |
| RU | 2564083 C2 * | 9/2015 | | A61F 5/445 |
| WO | WO-9318725 A1 * | 9/1993 | | A61F 5/448 |
| WO | WO-0135875 A2 * | 5/2001 | | A61F 5/448 |

OTHER PUBLICATIONS

International Search Report issued by ISA/EPO in connection with PCT/US2017/054903 dated Jan. 5, 2018.
Written Opinion issued by ISA/EPO in connection with PCT/US2017/054903 dated Jan. 5, 2018.

* cited by examiner

ADJUSTABLE CONVEXITY OSTOMY BARRIER

This is a National Stage Application of International Patent Application No. PCT/US2017/054903, filed Oct. 3, 2017, which claims the benefit of and priority to U.S. Provisional Application No. 62/403,449, filed Oct. 3, 2016, the entirety of which are incorporated fully herein by reference.

BACKGROUND

The following description generally relates to ostomy appliances, and in particular, to an ostomy barrier appliance.

Ostomy pouches for collecting bodily waste are used by individuals who have had surgery such as a colostomy, ileostomy, or urostomy. An ostomy pouch may be attached to a user via an ostomy barrier, which is configured to seal against peristomal skin surfaces and protect the peristomal surfaces from exposure to stomal effluent. However, the topography of stomas and peristomal surfaces surrounding stomas varies among patients, and sealing an ostomy appliance against such different peristomal surfaces and stomas remain as an area for further improvements. For example, a stoma may protrude more or less, or may even be flush or recessed.

A person with an ostomy having a stoma that is flush or recessed may find that applying external support or pressure from a barrier in the peristomal region aids in directing the discharge of effluent from the stoma directly into the ostomy pouch. Accordingly, the effectiveness of an adhesive seal between the ostomy barrier and the peristomal skin surface (i.e., a seal formed by the adhesive layer) may be prolonged. Thus, convex inserts and convex ostomy barriers, such as ADAPT® convex barrier rings available through the assignee of the present application, have been developed to apply pressure around such peristomal regions.

However, the convexity of a conventional convex ostomy barrier or insert is fixed and may not work efficiently for all ostomates. Thus, convex ostomy barriers and convex inserts of various convexity depths have been made available in the market. Further, an ostomate may wish to incrementally adjust the convexity of an ostomy barrier to achieve an optimal convexity for his/her topography of stoma.

Accordingly, it is desirable to provide an ostomy barrier having an adjustable convexity.

BRIEF SUMMARY

An ostomy barrier appliance including a skin barrier and a convexity adjusting device is provided according to various embodiments. The convexity adjusting device may be configured for incremental convexity adjustment of the skin barrier.

In one aspect, an ostomy barrier appliance for attaching an ostomy appliance to peristomal skin surrounding a stoma is provided according to an embodiment. The ostomy barrier appliance may include a skin barrier comprising an adhesive, an inlet opening defined in the skin barrier for receiving a stoma, and a convexity adjusting device arranged adjacent the skin barrier. The convexity adjusting device may be configured to adjust the convexity of the skin barrier.

The convexity adjusting device may include a fixed insert and an adjustable insert, and may be configured to adjust the convexity of the skin barrier by rotating the adjustable insert. In an embodiment, the fixed insert may include a plurality of female threads, while the adjustable insert includes a plurality of male threads. The male threads and female threads may be configured to engage each other, such that the adjustable insert may be threaded along an inner peripheral surface of the fixed insert to move in a transverse direction when rotated. In such an embodiment, a portion of the fixed insert may be attached to a pouch-facing surface of the skin barrier. As used herein, reference to transverse or transversely is transverse to a plane defined by the ostomy appliance.

In another embodiment, the fixed insert may include a transversely extending inner peripheral surface including a plurality of protrusions. The adjustable insert may include a wheel including a plurality of notches and a plurality spokes, in which the plurality spokes may be configured to extend transversely when the adjustable insert is rotated. The adjustable insert may be arranged adjacent the fixed insert, such that the plurality of protrusions are sitting in the plurality of the notches. In such an embodiment, the adjustable insert may be configured to rotate when a rotational force sufficient to slide the plurality of notches over the plurality of protrusions is applied. The adjustable insert may be further rotated to arrange the plurality of protrusions in the plurality of notches once again. The adjustable insert may also be configured to maintain the position and convexity of the skin barrier when the plurality of protrusions are arranged in the plurality of the notches.

Each of the spokes may be attached to the wheel and a flange of the adjustable insert via living hinges. Further, the ostomy barrier appliance may include a tape attached to an outer peripheral portion of the skin barrier. In such an embodiment, the fixed insert may include an outer flange, which is attached to an inner peripheral portion of the tape. The adjustable insert flange may be attached to the outer flange of the fixed insert adjacent the tape.

In some embodiments, the ostomy barrier appliance may include a support film arranged between the adjustable insert and the skin barrier, such that the adjustable insert may be rotated against the support film. The support film may be configured to reduce rotational friction, to thereby facilitate rotation of the adjustable insert against the support film. The adjustable insert may also include a plurality of lugs configured to facilitate rotation of the adjustable insert using a hand or a tool including a plurality of mating keys.

In another embodiment, the convexity adjusting device may include an inflatable bladder. The convexity adjusting device may be configured to increase a volume when a medium is inserted into the inflatable bladder. The skin barrier may be configured to protrude in a transverse direction to provide a convexity as the volume of the inflatable bladder increases. The inflatable bladder may include a valve, via which a medium may be insert into the inflatable bladder.

In yet another embodiment, the ostomy barrier appliance may include an air pump device with a pump tab. The air pump device may be configured to inflate a convexity adjusting device when pressure is applied to the pump tab.

In an embodiment, the convexity adjusting device may include a fixed insert comprising a first plurality of tooth-like structures, and an adjustable insert comprising a second plurality of tooth-like structures. The first and second plurality of tooth-like structures may be configured to engage each other, such that the adjustable insert slides down along the fixed insert toward the body-side of the ostomy barrier appliance when pressed down. The convexity adjusting device may also be configured to provide an asymmetric convexity. In such an embodiment, the convexity adjusting device may include a plurality of engagement sections, in which each of the engagement sections may include the first and second plurality of tooth-like structures. Each of the engagement section may be configured to be adjusted separately to provide a desired asymmetric convexity.

In yet another embodiment, the convexity adjusting device may include a convex insert receiving structure attached to a pouch-side surface of the skin barrier and a convex insert. The convex insert may be configured to be received in the convex insert receiving structure to provide the convexity of the skin barrier. In such an embodiment, the convexity of the skin barrier may be adjusted by selecting a convex insert having a desired depth.

In some embodiments, the ostomy barrier appliance may include a flange with a body-side coupling ring. The flange may be attached to a portion of the convexity adjusting device. The body-side coupling ring may be configured to mate with a pouch side coupling ring to attach an ostomy pouch to the ostomy barrier appliance.

An ostomy barrier appliance according to any of the foregoing embodiments may include a convexity adjusting device configured to provide a generally flat skin barrier, which is also configured to increase the convexity of the skin barrier incrementally to obtain a desired convexity. The ostomy barrier appliance may be configured to provide a convexity depth of the skin barrier of about 0 mm to about 15 mm, and/or a convexity angle of the skin barrier of about 0° to about 60°, wherein convexity angle=$\tan^{-1}$ (convexity depth/convexity width).

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
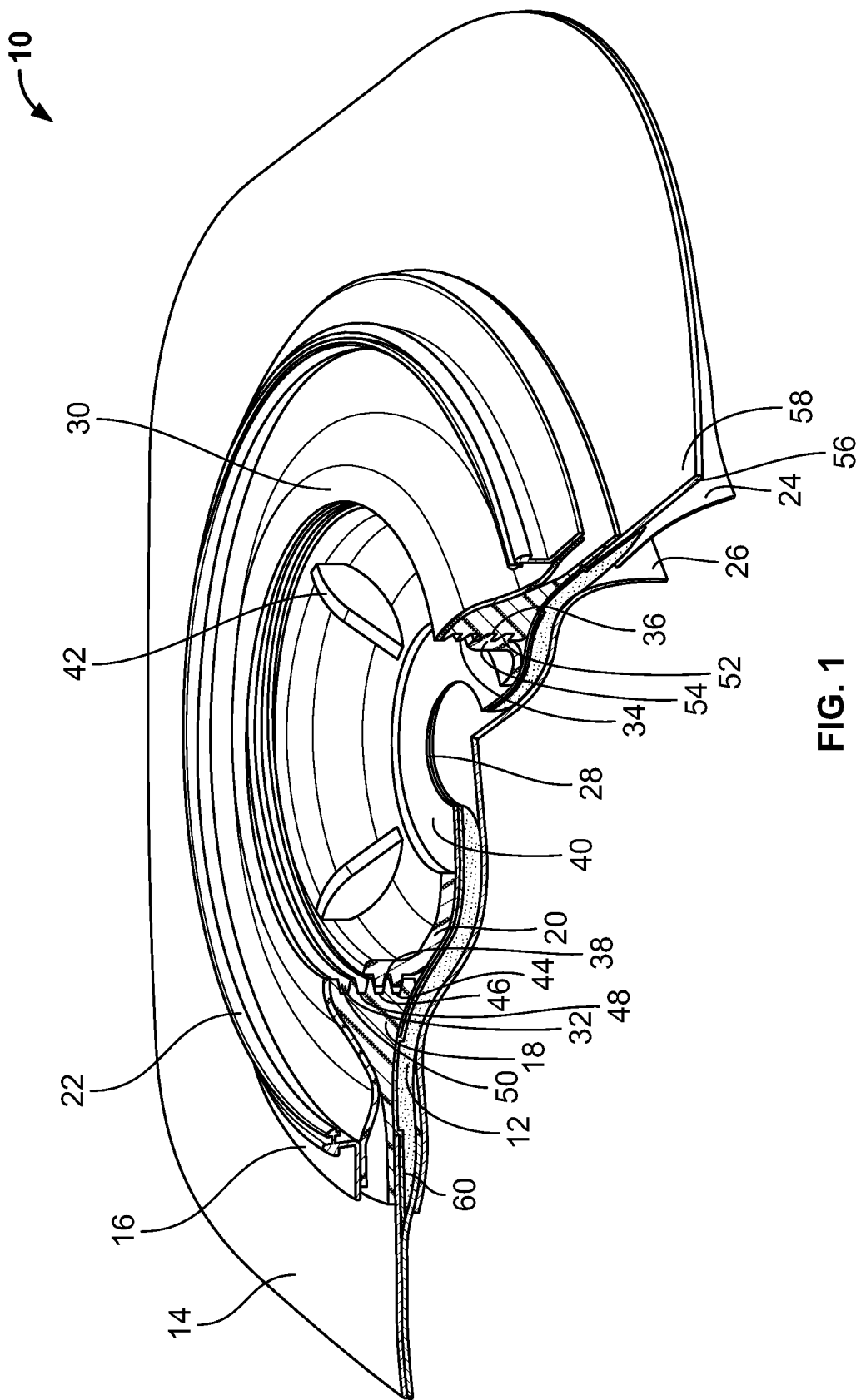
FIG. 1 is a perspective view of an ostomy barrier appliance according to an embodiment with a portion removed to illustrate its layered structure.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

An ostomy barrier appliance configured to provide a variable convexity is provided according to various embodiments. Referring to FIGS. 1-4, an ostomy barrier appliance 10 according to an embodiment is shown. FIG. 1 is a perspective view of the ostomy barrier appliance 10 with a portion removed and viewed from a pouch-facing side to illustrate a layered construction of the ostomy barrier appliance 10. The ostomy barrier appliance 10 may generally include a skin barrier 12, a flange 16, a convexity adjusting device 18, 20, release liners 24, 26, and an inlet opening 28 for receiving a stoma. The convexity adjusting device may include a fixed insert 18 and an adjustable insert 20, which are configured to adjust the convexity of the ostomy barrier appliance 10.

The flange 16 may include a body-side coupling ring 22 for attaching an ostomy appliance, such as an ostomy pouch. The body-side coupling ring 22 may be configured to mate with a pouch-side coupling ring (not shown), such that the ostomy pouch may be mechanically secured to the ostomy barrier appliance 10 when the coupling rings are engaged with each other. The flange 16 may be attached to the fixed insert 18 via a flange film 30. In the embodiment of FIG. 1, the flange 16 is attached to a pouch-facing surface of the flange film 30 proximate an outer periphery of the flange film 30. An inner peripheral portion of the fixed insert 18 is attached to a body-side surface of the flange film 30 proximate an inner peripheral portion of the flange film 30, such that the flange 16 and the fixed insert 18 are attached on the opposite surfaces of the flange film 30 at opposite ends. Such a configuration provides a floating flange feature, in which a user may insert his/her finger between the flange 16 and the fixed insert 18 to facilitate engagement of the coupling rings to attach a pouch to the ostomy barrier appliance 10.

The convexity adjusting device may include a fixed insert 18 and an adjustable insert 20, which are configured to mate with each other and cooperate to allow for adjusting the convexity of the ostomy barrier appliance 10. The fixed insert 18 may include a plurality of female threads 32 arranged on an inner peripheral surface 34. The adjustable insert 20 may be arranged adjacent the fixed insert 18 and include a plurality of male threads 36 on an outer peripheral surface 38. The plurality of female threads 32 and the plurality of male threads 36 are configured to engage each other, such that the adjustable insert 20 may be threaded along the inner peripheral surface 34 of the fixed insert 18. In such a configuration, the adjustable insert 20 may be threaded upward or downward in a transverse direction by rotating the adjustable insert 20 to adjust the convexity of the ostomy barrier appliance 10.

Figure 2:
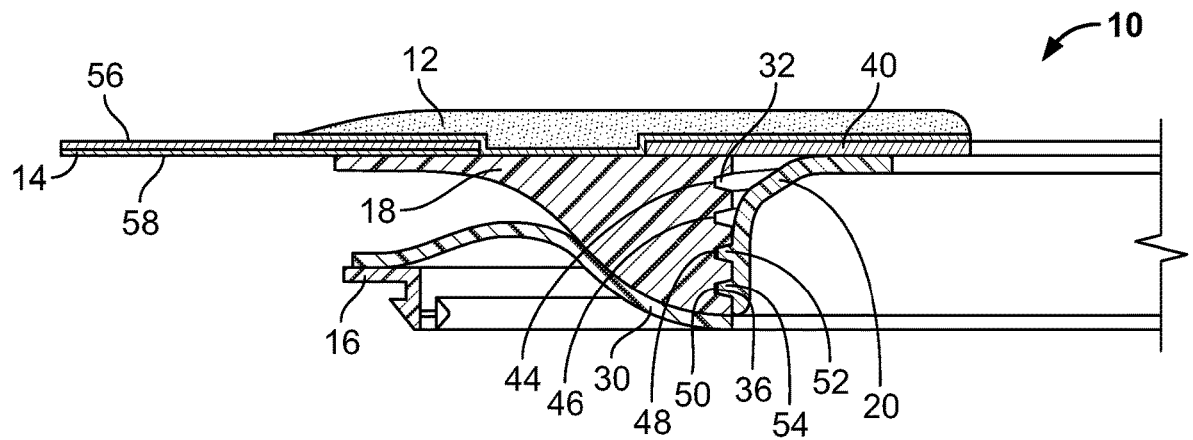
FIG. 2 is a schematic cross sectional view of the ostomy barrier appliance of FIG. 1 with release liners removed and illustrating a generally flat skin barrier.
Figure 3:
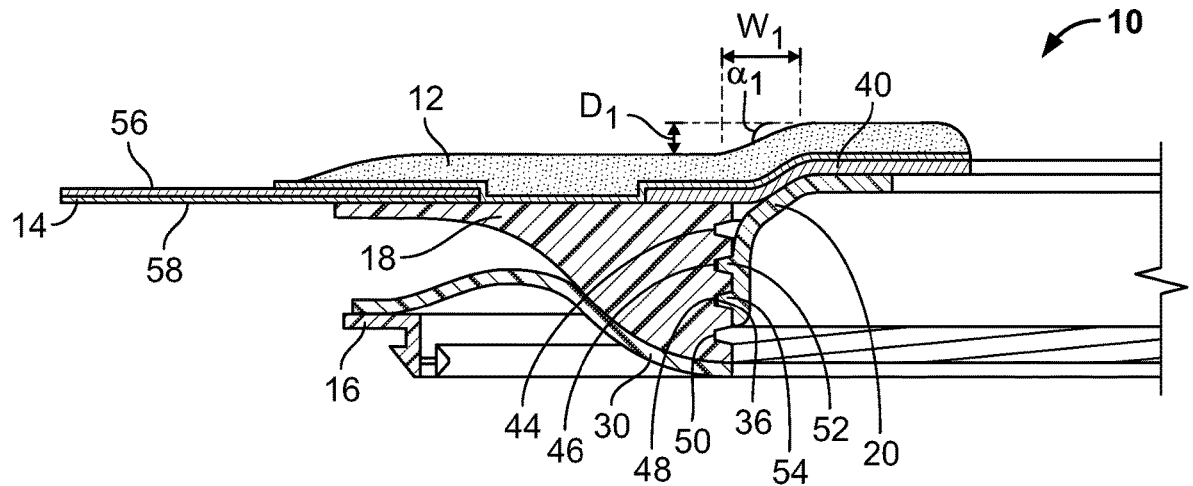
FIG. 3 is a schematic cross sectional view of the ostomy barrier appliance of FIG. 1 with release liners removed and illustrating an intermediate convexity of the skin barrier.
Figure 4:
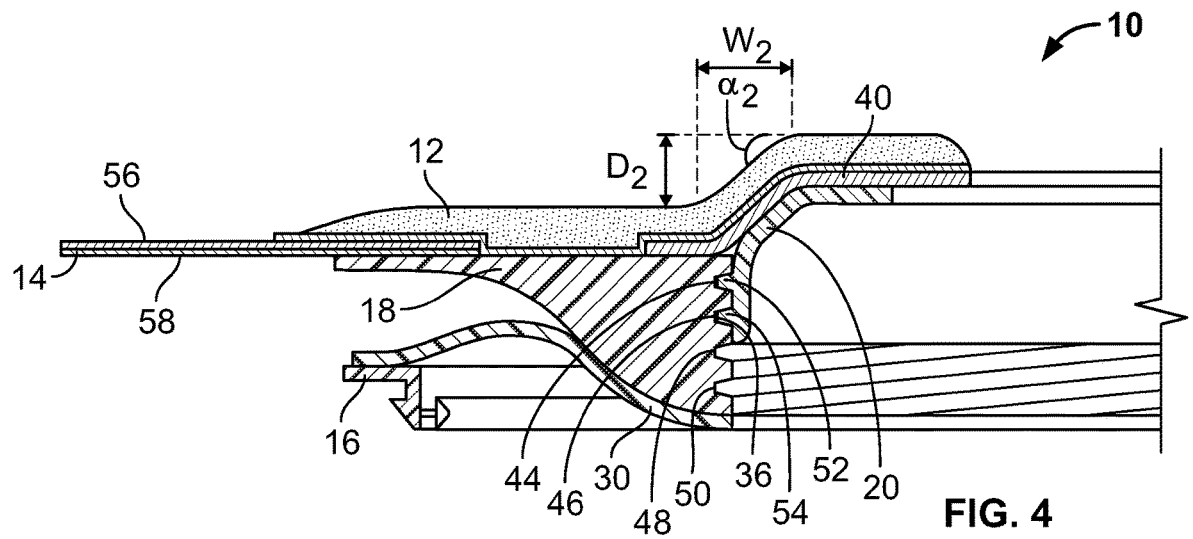
FIG. 4 is a schematic cross sectional view of the ostomy barrier appliance of FIG. 1 with release liners removed and illustrating a maximum convexity of the skin barrier.

In the embodiment of FIG. 1, the fixed insert 18 includes four female threads 44, 46, 48, 50, while the adjustable insert 20 includes two male threads 52, 54. FIGS. 2-4 are schematic cross-sectional views of the ostomy barrier appliance 10 with the release liners 24, 26 removed and illustrating various convexities obtained by adjusting the convexity adjusting device 18, 20. As shown, the inserts 18, 20 are configured for an incremental convexity adjustment of the ostomy barrier appliance 10.

In FIG. 2, the adjustable insert 20 is positioned such that the male threads 52, 54 are arranged in third and fourth female threads 48, 50 proximate a pouch-facing surface of the fixed insert 18 to provide a generally flat skin barrier 12. In FIG. 3, the adjustable insert 20 is threaded along the inner peripheral surface 34 of the fixed insert 18 by rotating the adjustable insert 20 and positioned, such that the male threads 52, 54 are arranged in second and third female threads 46, 48 to provide a convexity angle $\alpha_1$ of about 10° to about 40°, wherein convexity angle $\alpha_1 = \tan^{-1}$ (depth $D_1$/width $W_1$). In FIG. 4, the adjustable insert 20 is threaded further by a rotational motion and positioned, such that the male threads 52, 54 are arranged in first and second female threads 44, 48 to provide a greater convexity angle $\alpha_2$ of about 20° to about 60°, wherein convexity angle $\alpha_2 = \tan^{-1}$ (depth $D_2$/width $W_2$).

As the convexity angle $\alpha$ increases, the pressure applied to user's peristomal area by the ostomy barrier appliance also increases. The ostomy barrier appliance 10 allows for an incremental adjustment of the convexity to obtain the best barrier convexity to fit the topography of user's skin around the stoma and to provide a desired amount of pressure to the peristomal area for comfort and seal.

In other embodiments, the fixed insert 18 may include less than or more than four female threads, and the adjustable insert 20 may include one or more than two male threads. For example, the fixed insert 19 may include six female threads, and the adjustable insert 20 may include two male threads to allow for a smaller incremental convexity adjustment and/or a greater convexity depth and angle. In some embodiments, the threads may be reversed, wherein the fixed insert may include male threads while the adjustable insert includes male threads.

Figure 5:
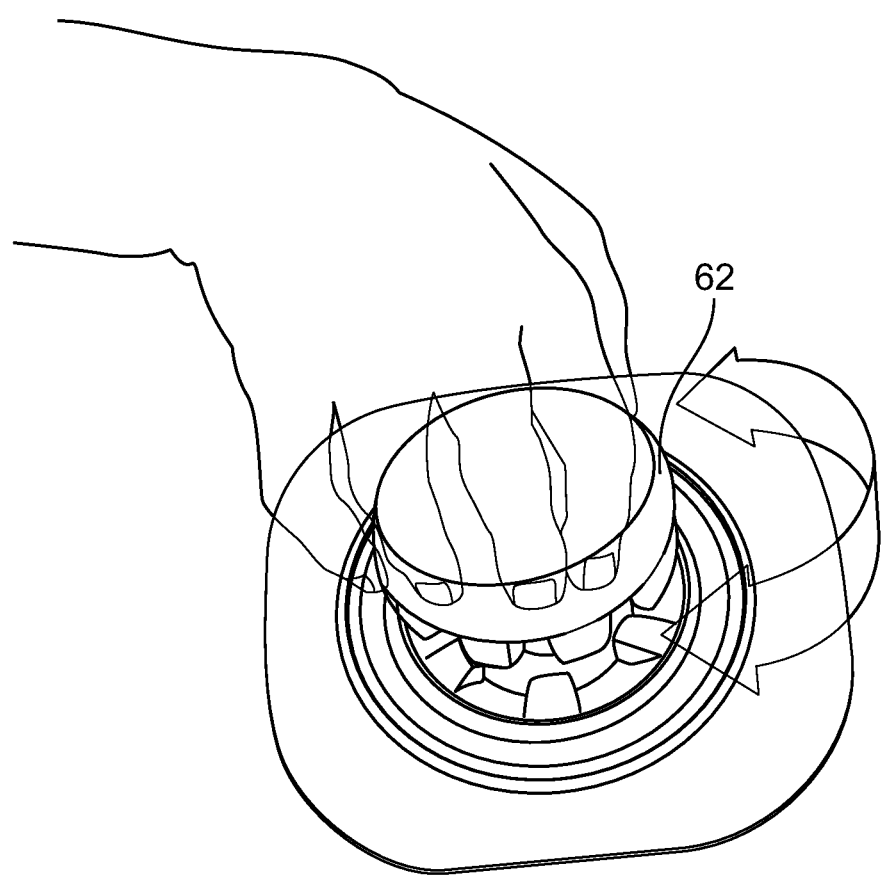
FIG. 5 is a perspective view of an ostomy barrier appliance with a rotating tool according to an embodiment.

In an embodiment, the adjustable insert 20 may include a plurality of lugs 42 to facilitate rotation of the adjustable insert 20. A user may rotate the adjustable insert 20 using a hand by grabbing or pushing against the lugs 42 or using a tool 62 including keys to engage the lugs 42 as shown in FIG. 5.

The skin barrier 12 is arranged on the body-side surface of the ostomy barrier appliance 10 for attachment to a user. The inlet opening 28 may be defined by an inner periphery of the skin barrier 12 for receiving a stoma (not shown.) At least a portion of skin barrier 12 may be secured to the fixed insert 18.

The skin barrier 12 may be formed from a suitable medical-grade adhesive that can adhesively secure the ostomy barrier appliance 10 to a patient's skin in the peristomal region, such as a hydrocolloid adhesive composition.

In the embodiment of FIGS. 1-4, the ostomy barrier appliance 10 also includes a tape 14 including an adhesive layer 56 and a backing layer 58. The tape 14 may be attached to a pouch-facing surface of the skin barrier 12 proximate its outer periphery, such that the backing layer 58 is arranged on the pouch-facing surface of the ostomy barrier appliance 10, while the adhesive layer 56 may adhere to the patient's skin to provide additional security.

The adhesive layer 56 may be formed from a suitable medical adhesive, such as an acrylic adhesive. The backing layer 58 may be formed from a suitable material, such as a nonwoven material or a thin polymeric film.

In other embodiments, the ostomy barrier appliance 10 may not include the tape 14. In such an embodiment, the skin barrier 12 may be the only means for attaching the ostomy barrier appliance 10 to a user.

The ostomy barrier appliance 10 may also include a support film 40. The support film 40 may be provided on the pouch-facing surface of the skin barrier 12 in an inner peripheral portion, such that the adjustable insert 20 may sit on the support film 40 as shown in FIG. 1. The support film 40 may be formed from a suitable polymeric material to facilitate rotation of the adjustable insert 20. For example, the support film 40 may be formed from a plastic film having a low surface energy to minimize friction between the support film 40 and the adjustable insert 20 when adjustable insert 20 is rotated against the support film 40.

In an embodiment, the skin barrier 12 may include a backing layer 60 laminated on the pouch-facing surface of the skin barrier 12. The backing layer 60 may be formed from a suitable heat sealable polymeric material, such that the tape 14 may be heat sealed to the backing layer 60 proximate the outer periphery of the skin barrier 12. The fixed insert 18 and the support film 40 may also be heat sealed to the backing layer 60. In another embodiment, the backing layer 60 may be formed from a suitable heat sealable polymeric material having a sufficiently low surface energy to minimize friction between the backing layer 60 and the adjustable insert 20 when the adjustable insert 20 is rotated. In such an embodiment, the ostomy barrier appliance 10 may not include a support film 40, and the backing layer 60 may function as a support film.

A release liner may be provided to cover the skin barrier 12 and the tape 14. In the embodiment of FIG. 1, the release liner 26 is provided to cover the skin barrier 12, and the release liner 24 is provided to cover the tape 14 and an outer peripheral portion of the skin barrier 12 for easy handing and positioning of the ostomy barrier appliance 10. In use, the release liner 26 may be removed first for attachment of the skin barrier 12 to peristomal skin, and the release liner 24 may be removed subsequently to expose the tape for further attachment to user's skin.

Figure 6:
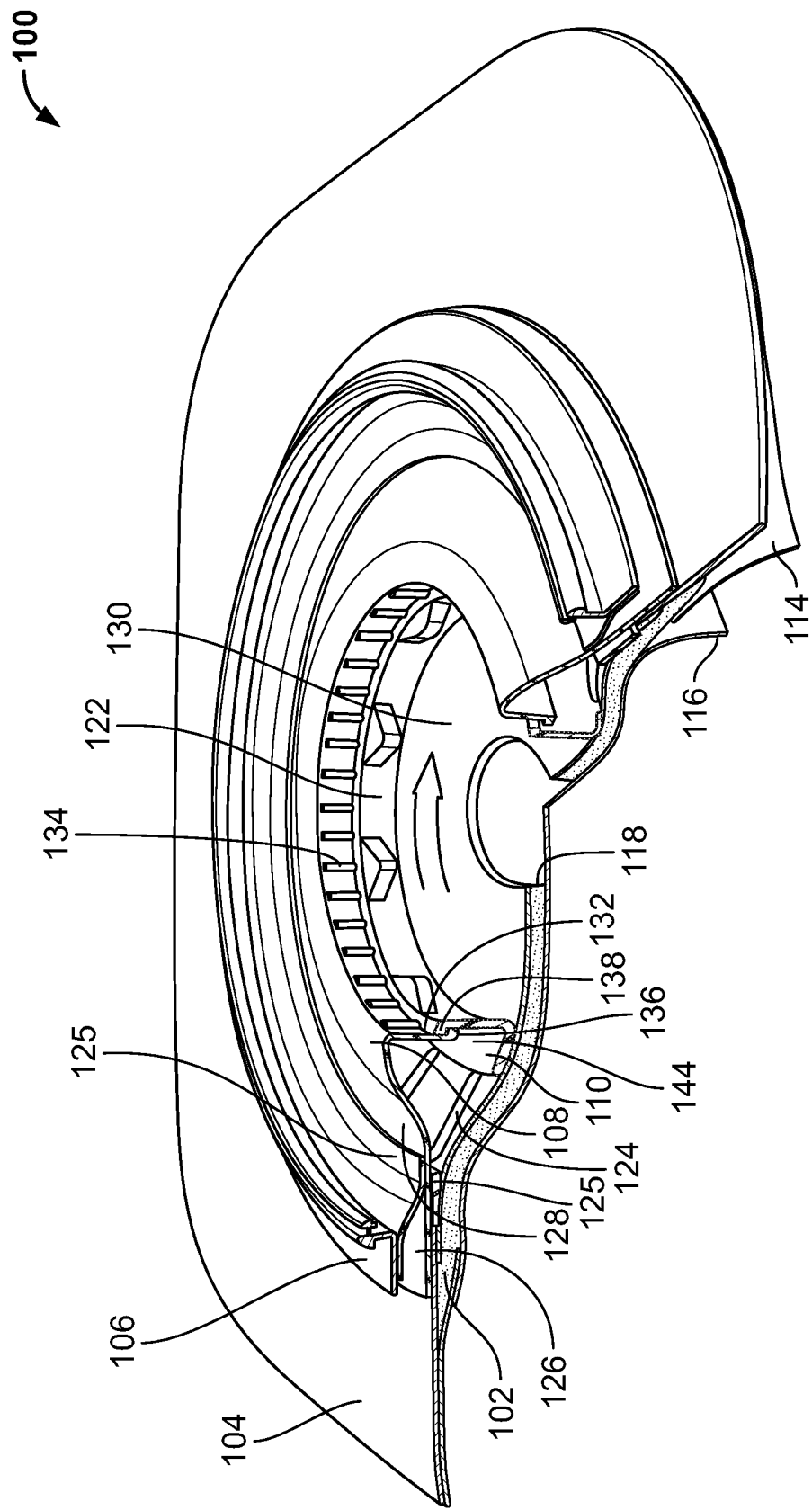
FIG. 6 is a perspective view of an ostomy barrier appliance according to another embodiment with a portion removed to illustrate its layered structure.
Figure 7:
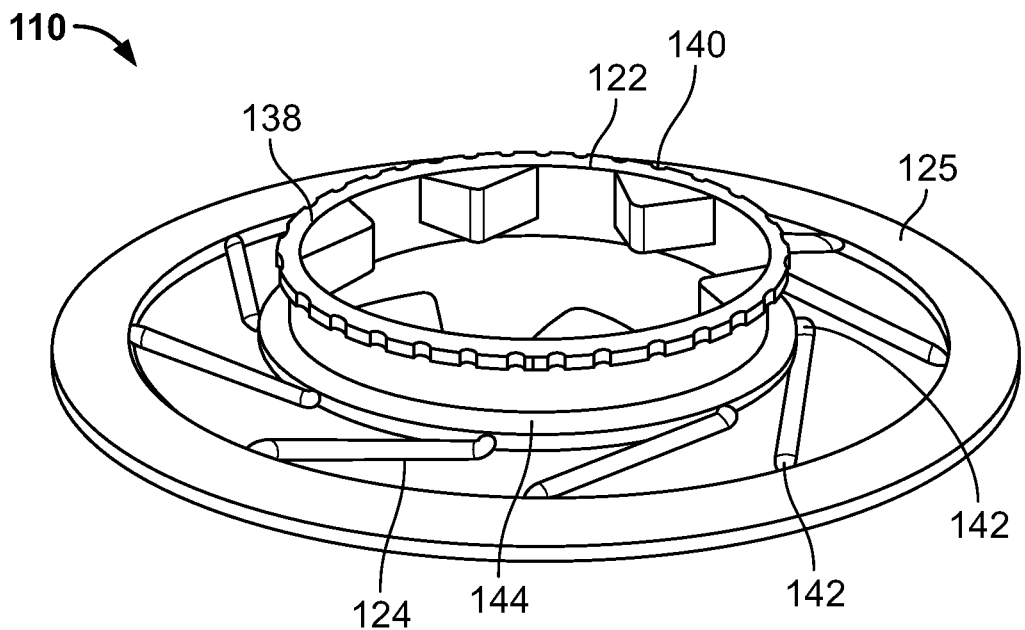
FIG. 7 is a perspective view of a convexity adjusting device of the ostomy barrier appliance of FIG. 6 including a wheel and spokes.
Figure 8:
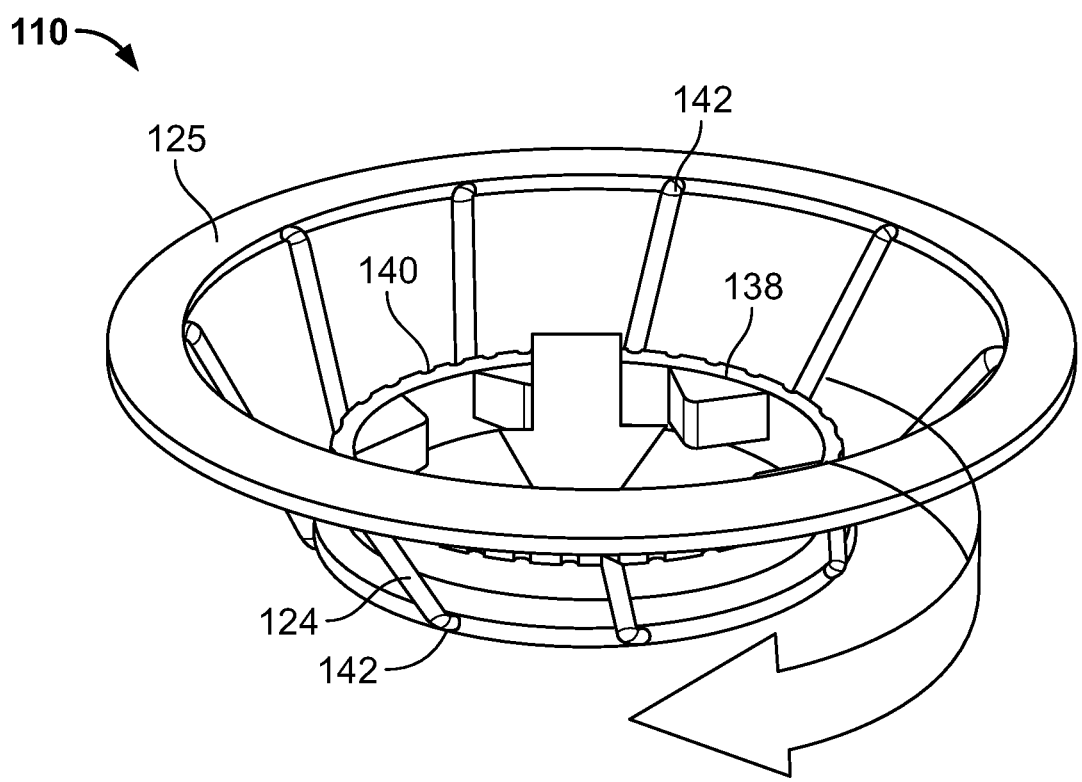
FIG. 8 is a perspective view of the convexity adjusting device of FIG. 7 with the spokes extended.

FIGS. 6-8 show an ostomy barrier appliance 100 according to another embodiment. FIG. 6 is a perspective view of the ostomy barrier appliance 100 with a portion removed and viewed from a pouch-facing side to illustrate a layered construction of the ostomy barrier appliance 100. The ostomy barrier appliance 100 may be similarly constructed to the ostomy barrier appliance 10 generally including a skin barrier 102, a tape 104, a flange 106, a convexity adjusting device 108, 110, release liners 114, 116, a support film 130, and an inlet opening 118 for receiving a stoma. In this embodiment, the convexity adjusting device 108, 110 is constructed differently than the convexity adjusting device 18, 20 of the embodiment of FIG. 1

The convexity adjusting device of this embodiment may include a fixed insert 108 and an adjustable insert 110 including a wheel 122 and a plurality of spokes 124. The fixed insert 108 may include a flange 126 and a sloped portion 128 extending from the flange 126 toward the inlet opening 118, and an inner surface 132 transversely extending from the sloped portion 128 toward the skin barrier 102. The inner surface 132 may include a plurality of protrusions 134 transversely extending along the inner surface 132, and a bottom rim 136 extending radially toward the inlet opening 118. An outer peripheral portion of the flange 126 may be attached to a pouch-facing surface of the tape 104 proximate inner periphery of the tape 104 as shown in FIG. 6.

The adjustable insert 110 may include the wheel 122, a flange 125 and the plurality of spokes 124 extending between the wheel 122 and the flange 125. The wheel 122 may include an upper rim 138 including a plurality of notches 140 and a lower rim 144. The flange 125 of the adjustable insert 110 may be attached to the flange 126 of the fixed insert 108 as shown in FIG. 6. The plurality of the protrusions 134 and the plurality of notches 140 are configured to engage each other, such that the wheel 122 may be arranged adjacent the inner surface 132 of the fixed insert 108 with the plurality of the protrusions 134 sitting in the plurality of notches 140 as shown in FIG. 6.

Each of the plurality of spokes 124 may be attached to the wheel 122 and the flange 125 via living hinges 142, which are configured to transversely extend the spoke 124 when the wheel 122 is rotated as shown in FIGS. 7 and 8. Similar to the convexity adjustment device 18, 20, the fixed insert 108 and the adjustable insert 110 are configured for incremental adjustment of the convexity of the ostomy barrier appliance 100. In an embodiment, a generally flat skin barrier 102 may be provided when the plurality of spokes 124 are extended radially, and the lower rim 144 and the flange 125 of the adjustable insert 110 are arranged generally on a same plane as shown in FIG. 7. In this position, the fixed insert 108 and the adjustable insert 110 may be arranged, such that the lower rim 144 of the adjustable insert 110 may butt against the bottom rim 136 of the fixed insert 108 to prevent further movement of the adjustable insert 110 toward the pouch side.

To adjust the convexity, the adjustable insert 110 may be rotated by applying sufficient rotational force to slide the plurality of the notches 140 over the plurality of protrusions 134 to move them out of an engaged position. The adjustable insert 110 may be further rotated to slide the plurality of the notches 140 over the plurality of protrusions 134 again to move them back into an engaged position. In such an embodiment, the convexity of the ostomy barrier appliance may be securely maintained when the plurality of notches 140 and the plurality of protrusions 134 are in an engaged position. As such, an incremental adjustment of the convexity is made possible. A maximum convexity of the ostomy barrier appliance 100 may be provided when the wheel 122 is rotated to transversely extend the plurality of spokes 124, such that the upper rim 138 of the adjustable insert 110 is arranged against the bottom rim 136 of the fixed insert 108 as shown in FIGS. 6 and 8.

Figure 9:
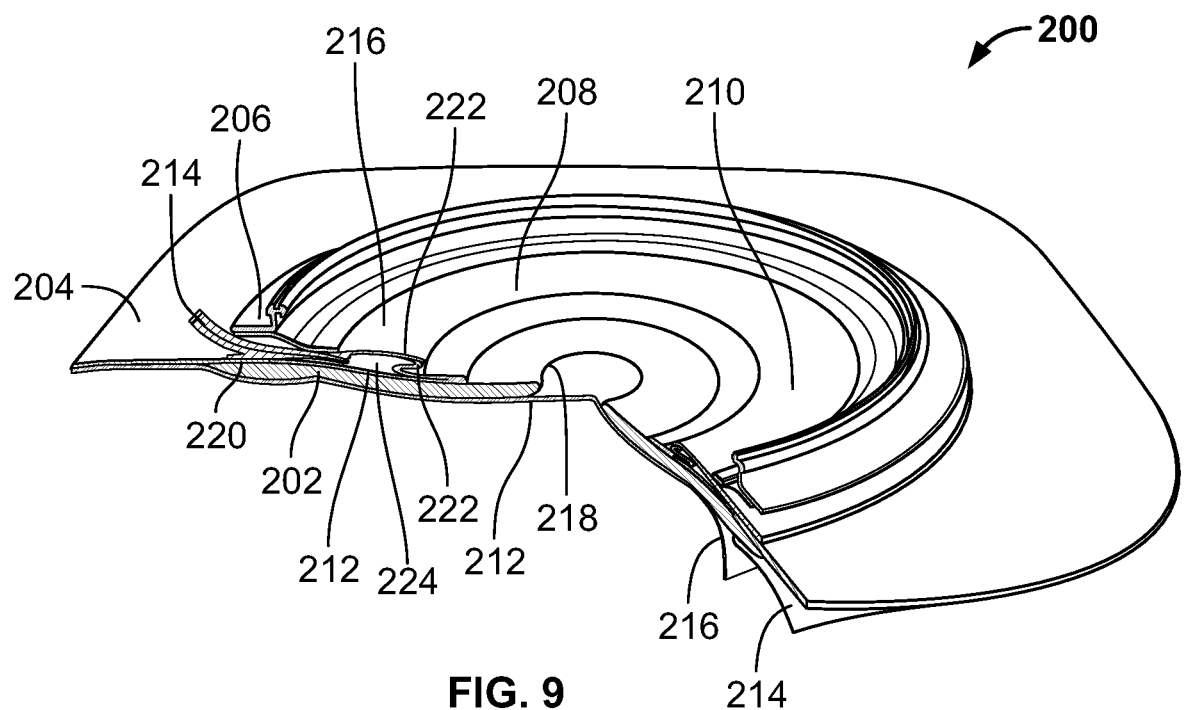
FIG. 9 is a perspective view of an ostomy barrier appliance according to yet another embodiment with a portion removed to illustrate its layered structure and providing a generally flat skin barrier.
Figure 10:
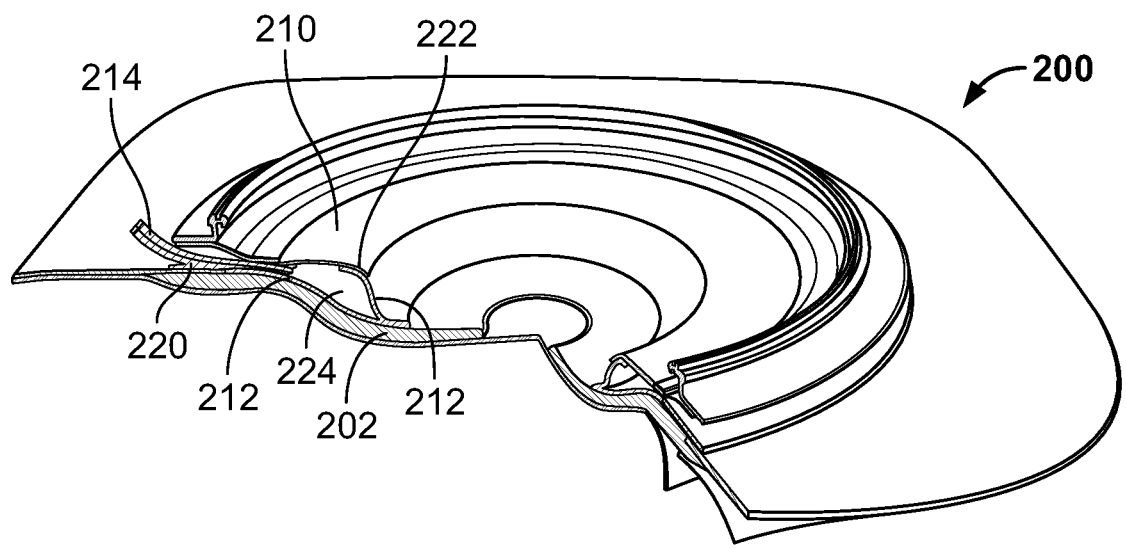
FIG. 10 is a perspective view of an ostomy barrier appliance of FIG. 9 providing a convex skin barrier.
Figure 11:
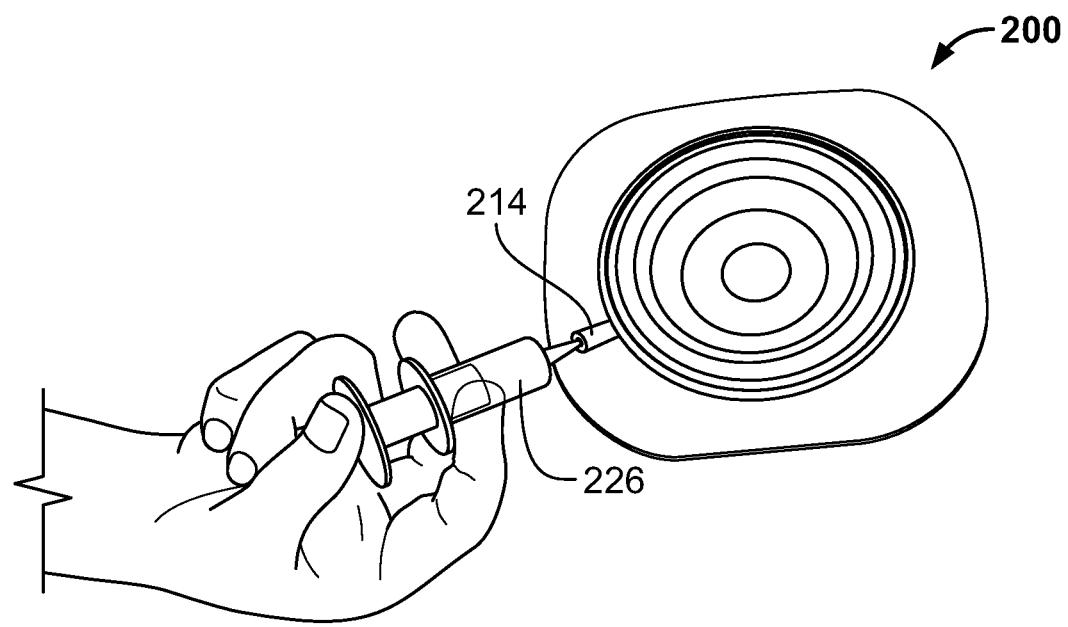
FIG. 11 is a perspective view of the ostomy barrier appliance of FIG. 9 with a syringe for inserting a gas medium to inflate a convexity adjusting device.

FIGS. 9-11 show an ostomy barrier appliance 200 according to another embodiment. FIG. 9 is a perspective view of the ostomy barrier appliance 200 with a portion removed and viewed from a pouch-facing side to illustrate a layered construction of the ostomy barrier appliance 200. The ostomy barrier appliance 200 may be similarly constructed to the ostomy barrier appliances 10, 100 generally including a skin barrier 202, a tape 204, a flange 206, a convexity adjusting device 208, release liners 214, 216, and an inlet opening 218 for receiving a stoma. In this embodiment, the convexity adjusting device 208 may be an inflatable bladder.

The convexity adjusting device 208 may comprise a top portion 210 and a bottom portion 212. The top portion 210 includes a valve 214 proximate the outer periphery and a flange portion 216. An outer peripheral portion 220 of the top portion 210 may be attached to the tape 204 and an inner peripheral portion 222 is sealed to the bottom portion 212. A portion of the bottom portion 212 is attached to the skin barrier 202. Together, the top portion 210 and the bottom portion 212 define an inflatable bladder 224. The top and bottom portions 210, 212 may be formed from a suitable material such as polymeric material or rubber. In another embodiment, the top and bottom portions 210, 212 may be integrally formed from a one continuous piece of a suitable material.

In FIG. 9, the inflatable bladder 224 is deflated to provide a generally flat skin barrier 202. In FIG. 10, the inflatable bladder 224 is inflated to provide convexity to the skin barrier 202. The ostomy barrier appliance 200 may be inflated by inserting a medium, such as a gas, liquid, or solid, into the inflatable bladder 224. As the medium enters the inflatable bladder 224, the volume of the inflatable bladder 224 increases and causes a portion of the skin barrier 202 adjacent the inflatable bladder 224 to protrude in the transverse direction to increase a depth of the convexity, thereby increasing pressure applied to the peristomal skin of a user. A user may adjust the convexity of the skin barrier 202 by adjusting a quantity of the medium inserted into the inflatable bladder 224.

Figure 12:
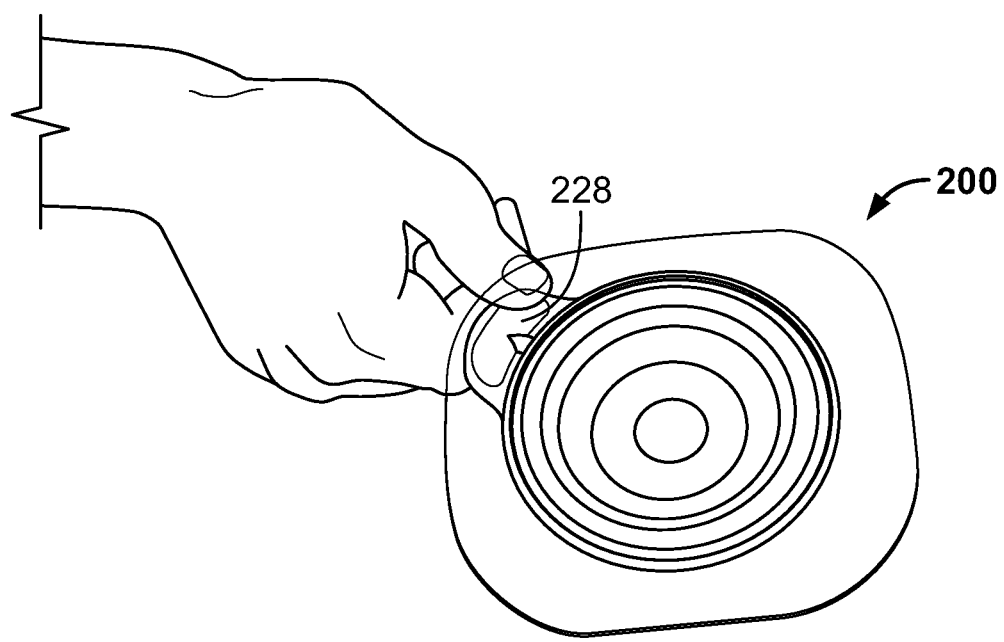
FIG. 12 is a perspective view of an ostomy barrier appliance including an air pump device according to an embodiment.

The medium may be inserted into the inflatable bladder 224 using different means. In an embodiment, a gas medium, such as air, may be inserted using a syringe 226 through the valve 214 into the bladder 224 as shown in FIG. 11. In another embodiment, the ostomy barrier appliance 200 may include an air pump device, in which a user may press a pump tab 228 to inflate an inflatable convexity adjusting device as shown in FIG. 12.

Figure 14:
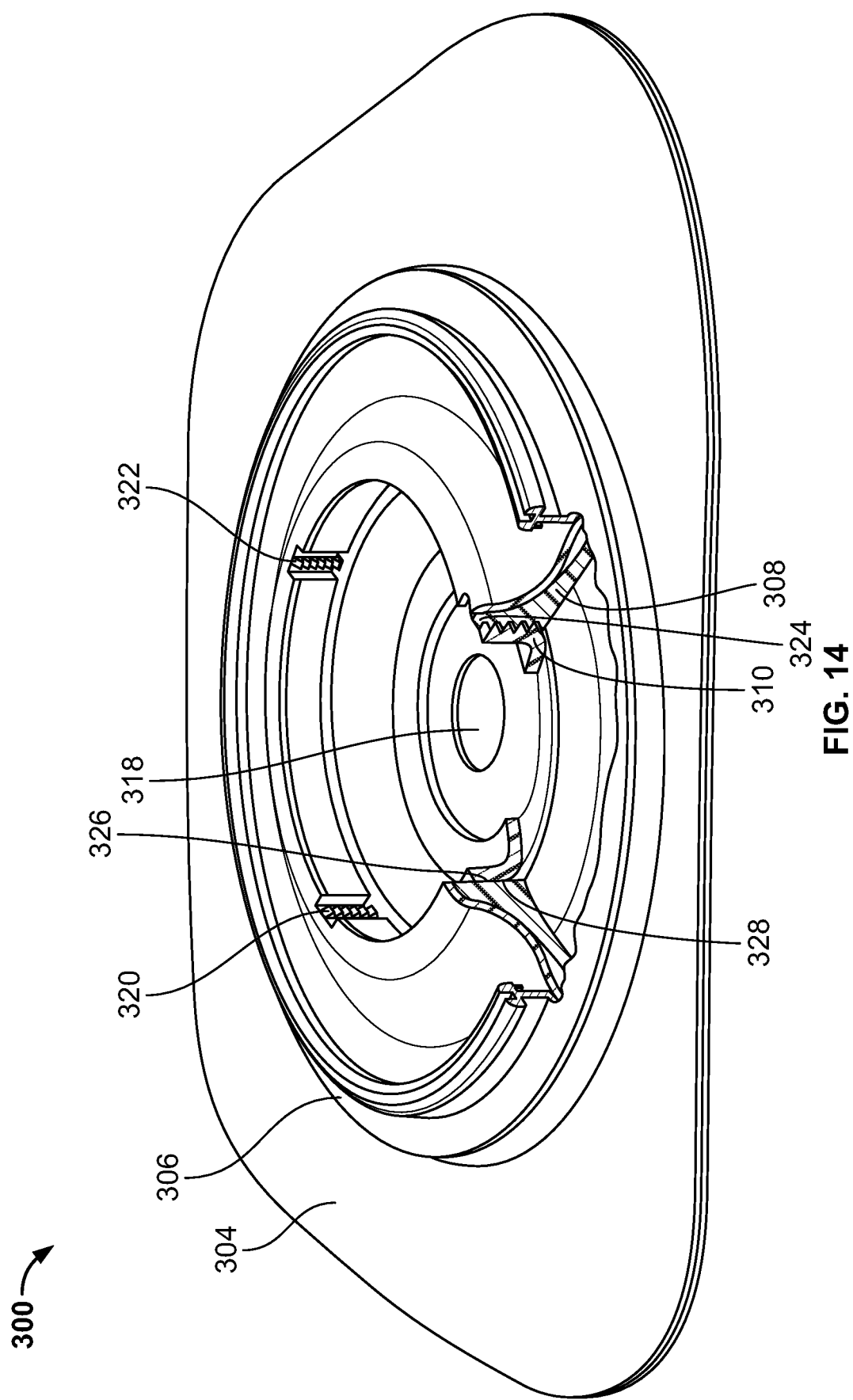
FIG. 14 is a perspective view of an ostomy barrier appliance according to an embodiment with a portion removed.
Figure 15:
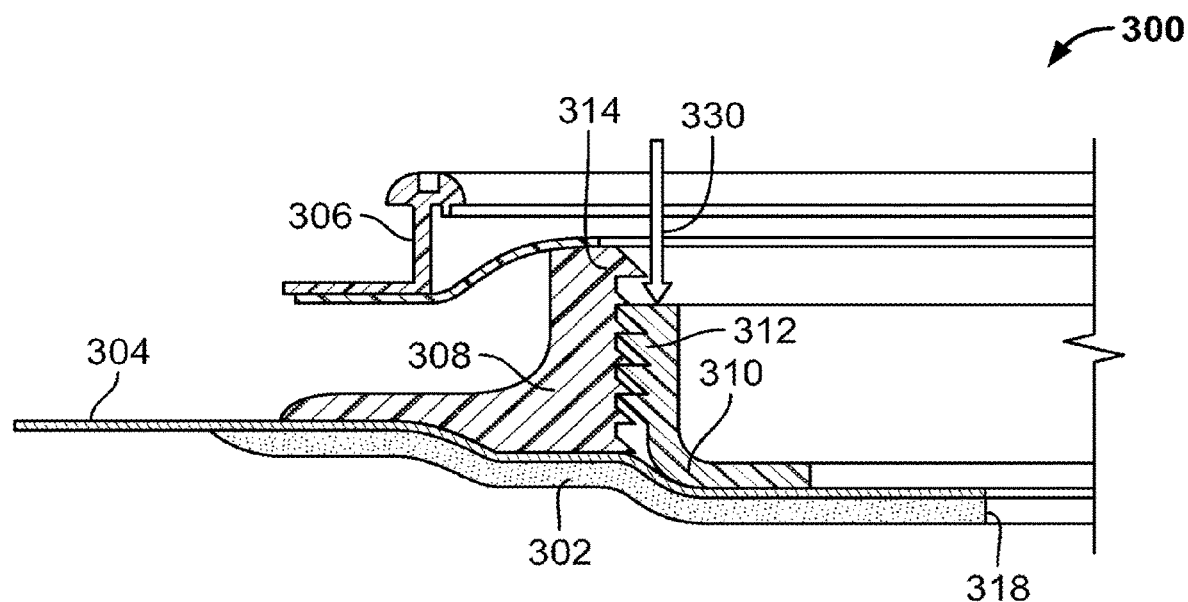
FIG. 15 is a schematic cross sectional view of the ostomy barrier appliance of FIG. 14.

FIGS. 14 and 15 show an ostomy barrier appliance 300 according to yet another embodiment. The ostomy barrier appliance 300 may be similarly constructed to the ostomy barrier appliance 10 generally including a skin barrier 302, a tape 304, a flange 306, a convexity adjusting device including a fixed insert 308 and an adjustable insert 310, and an inlet opening 318 for receiving a stoma. In this embodiment, the convexity adjusting device may be configured to adjust the convexity of the ostomy barrier appliance 300 by pushing down on the adjustable insert 310 toward a body-side direction 330 (FIG. 15).

The adjustable insert 310 may include a plurality of sawtooth-like structure 312. The fixed insert 308 may be configured to mate with the adjustable insert 310 including a plurality of tooth-like structure 314. An engagement mechanism between the fixed insert 308 and the adjustable insert 310 may be configured similar to a cable tie, in which the plurality of sawtooth-like structure of the adjustable insert 310 may be pushed down toward the body-side direction 330 along the plurality of tooth-like structure 314 of the fixed insert 308. In such an embodiment, the adjustable insert 310 may be configured to slide down along the fixed insert 308 toward the body-side 330, but prevented from sliding back up toward a pouch-side.

The ostomy barrier appliance 300 may be configured to provide an asymmetric convexity as shown in FIG. 14. In this embodiment, the convexity adjusting device 308, 310 includes three engagement sections 320, 322, 324 including the mating tooth-like structures 312, 314. The rest of the inner peripheral surface 326 of the fixed insert 308 and the outer peripheral surface 328 of the adjustable insert 310 may be smooth without any tooth-like structures as shown in FIG. 14. In such an embodiment, each of the engagement portions 320, 322, 324 may be adjusted and fixed at a different location along the fixed insert 308 to provide a different convexity height, thereby providing an asymmetric convexity. In other embodiments, the ostomy barrier appliance 300 may include one or two engagement sections, or more than three engagement sections.

Figure 16:
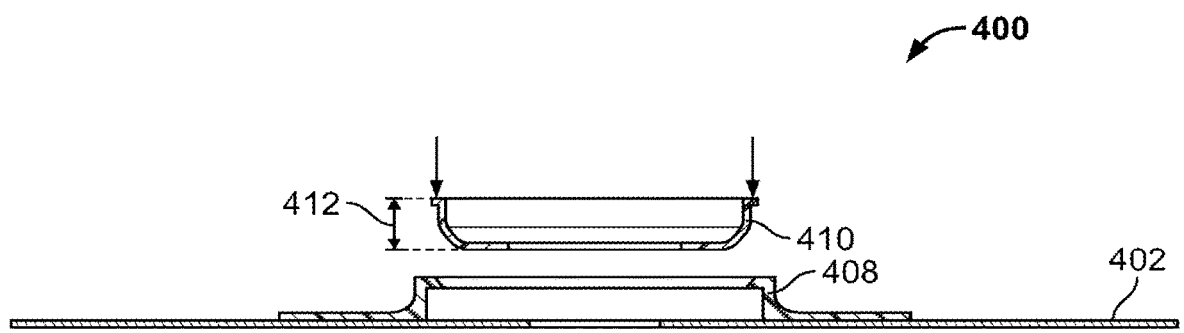
FIG. 16 is a schematic cross sectional view of an ostomy barrier appliance including a convex insert according to an embodiment.

FIG. 16 is a schematic cross sectional view of an ostomy barrier appliance 400 according to yet another embodiment. The ostomy barrier appliance 400 generally comprises a skin barrier 402, a convex insert receiving structure 408, and a convex insert 410. The convex insert receiving structure 408 may be attached to a pouch-side surface of the skin barrier 402. The convex insert 410 may be configured to be received and fixed in the convex insert receiving structure 408 to provide a convexity. The convex inserts 410 may be provided to have various different depths 412 for different convexity. The convex inserts 410 may be formed from various different materials having different softness. In use, a user may select from a number of different convex inserts 410, each of which may be configured to have a different depth 410 or/and different softness, to obtain a desired convexity and softness of the ostomy barrier appliance 400.

Figure 13A:
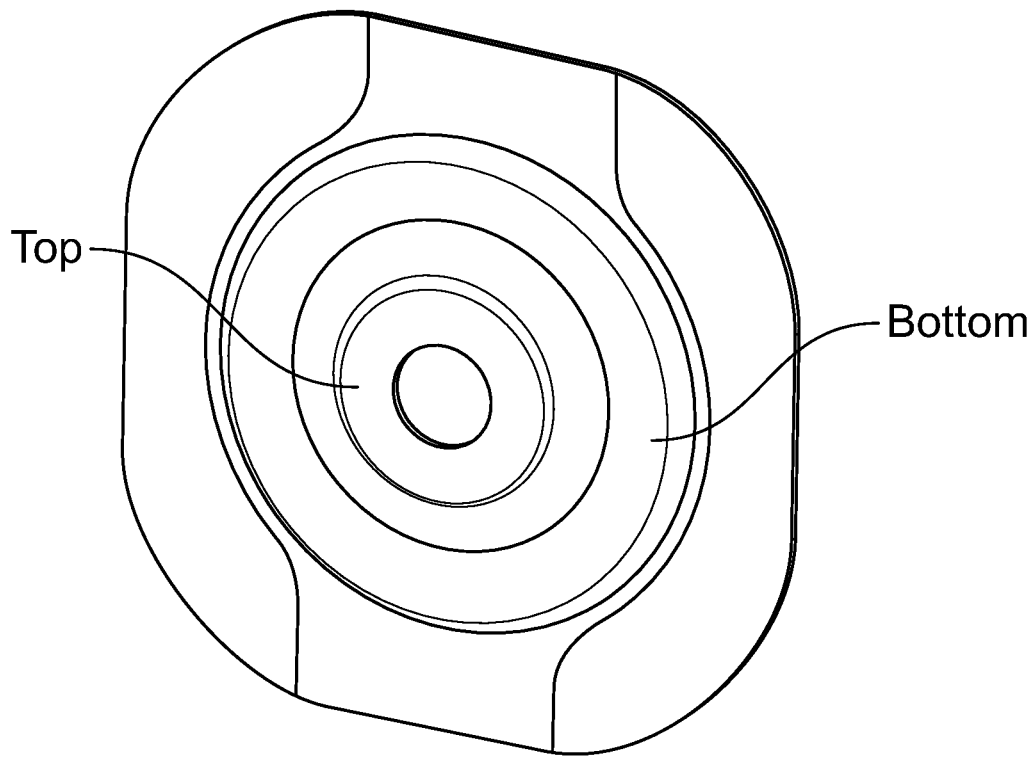
FIGS. 13A and 13B are schematic illustrations to show the convexity width, convexity depth, and convexity angle of a convex ostomy barrier according to an embodiment.
Figure 13B:
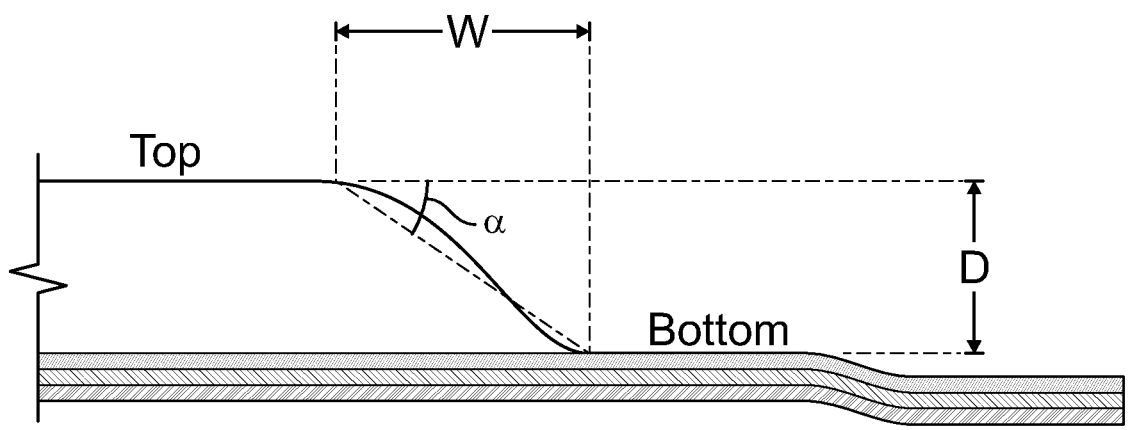

The ostomy barrier appliances according to various embodiments of the present disclosure may be configured to provide a convexity depth W of about 0 mm to about 15 mm, preferable about 0 mm to about 12 mm, and more preferably about 0 mm to about 10 mm, and a convexity angle α of about 0° to about 60°, preferably about 0° to about 50°, more preferably about 0° to about 40°, wherein $\alpha=\tan^{-1}$ (depth D/width W). A convexity angle α, depth D, and width W are illustrated in FIGS. 13A and 13B.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy barrier appliance for attaching an ostomy appliance to a peristomal skin surrounding a stoma, the ostomy barrier appliance comprising: a skin barrier comprising an adhesive; an inlet opening defined in the skin barrier for receiving a stoma; and a convexity adjusting device arranged adjacent the skin barrier; wherein the convexity adjusting device is configured to adjust a convexity and softness of the ostomy barrier appliance, wherein the convexity adjusting device includes a convex insert receiving structure attached to a pouch-side surface of the skin barrier and a plurality of convex inserts, wherein each of the plurality of convex inserts is configured to be received in the convex insert receiving structure and make contact with the skin barrier to provide the convexity and softness of the ostomy barrier appliance, wherein the convexity and softness of the ostomy barrier appliance are adjusted by selecting one of the plurality of the convex inserts having a desired depth and softness, wherein the plurality of convex inserts includes a first convex insert formed from a first material and a second convex insert formed from a second material, wherein the first material has a different softness than the second material.

2. The ostomy barrier appliance of claim 1, wherein the ostomy barrier appliance includes a flange with a body-side coupling ring, wherein the flange is attached to a portion of the convexity adjusting device, wherein the body-side coupling ring is configured to mate with a pouch side coupling ring to attach an ostomy pouch to the ostomy barrier appliance.

3. The ostomy barrier appliance of claim 1, wherein the convexity adjusting device is configured to provide a generally flat skin barrier and to increase the convexity of the skin barrier incrementally and to set the convexity of the skin barrier at a desired convexity.

4. The ostomy barrier appliance of claim 1, wherein the ostomy barrier appliance is configured to provide a convexity depth of the skin barrier of about 0 mm to about 15 mm.

5. The ostomy barrier appliance of claim 1, wherein the ostomy barrier appliance is configured to provide a convexity angle of the skin barrier of about 0° to about 60°, wherein convexity angle=$\tan^{-1}$(convexity depth/convexity width).

\* \* \* \* \*